US006373963B1

United States Patent
Demers et al.

(10) Patent No.: US 6,373,963 B1
(45) Date of Patent: Apr. 16, 2002

(54) SYSTEMS, METHODS AND COMPUTER PROGRAM FOR MEASURING THE SURFACE CONTOUR OF AN OBJECT

(75) Inventors: Michelle H. Demers, New Hill; Richard Wulpern, Sanford; Jeffery Hurley, Cary, all of NC (US); John R. Grindon, Hazelwood, MO (US)

(73) Assignee: Textile/Clothing Technology Corporation, Cary, NC (US)

( * ) Notice: Subject to any disclaimer, the term of this patent is extended or adjusted under 35 U.S.C. 154(b) by 0 days.

(21) Appl. No.: 09/241,708

(22) Filed: Feb. 2, 1999

Related U.S. Application Data

(60) Provisional application No. 60/073,776, filed on Feb. 5, 1998.

(51) Int. Cl.[7] .................................................. G06K 9/00
(52) U.S. Cl. ..................................... 382/108; 108/100
(58) Field of Search ................................ 382/108, 154; 356/600, 603, 604, 605; 355/53

(56) References Cited

U.S. PATENT DOCUMENTS

| | | | | |
|---|---|---|---|---|
| 4,442,842 A | * | 4/1984 | Baba .......................... | 600/463 |
| 4,525,858 A | * | 6/1985 | Cline et al. ................. | 382/154 |
| 4,641,972 A | * | 2/1987 | Halioua et al. ............. | 356/376 |
| 4,802,759 A | * | 2/1989 | Matsumoto et al. ........ | 356/603 |
| 4,846,577 A | | 7/1989 | Grindon ...................... | 356/376 |
| 4,871,256 A | | 10/1989 | Grindon ...................... | 356/376 |
| 5,075,562 A | * | 12/1991 | Greivenkamp, Jr. et al. ..... | 250/559.05 |
| 5,561,526 A | * | 10/1996 | Huber et al. ................. | 356/376 |
| 5,612,181 A | * | 3/1997 | Fourmentin-Guilbert ....... | 435/6 |
| 5,825,495 A | * | 10/1998 | Huber ......................... | 356/600 |
| 5,991,004 A | * | 11/1999 | Wallace et al. ............... | 355/53 |
| 6,147,760 A | * | 11/2000 | Geng .......................... | 356/376 |

* cited by examiner

*Primary Examiner*—Leo Boudreau
*Assistant Examiner*—Abolfazl Tabatabai
(74) *Attorney, Agent, or Firm*—Myers Bigel Sibley & Sajovec

(57) ABSTRACT

Systems methods and computer program products are provided for obtaining a three-dimensional data set that is representative of a surface of a three-dimensional object. A grating pattern, having a sinusoidally varying intensity pattern, is projected onto the surface of an object. The projected grating pattern is shifted a number of times and two-dimensional deformed grating images of an area segment of the object surface are captured and stored. A two-dimensional array of optical phase values is then created. Optical phase values in the two-dimensional array are then used to generate a plurality of three-dimensional data points that represent respective points on the surface of the object. Each three-dimensional data point is found by locating, for each pixel in the detector array of pixels, a point on the surface of the object wherein a ray from a respective pixel passing through a nodal point of a detector lens is intersected by a plane of constant phase from the projected first grating pattern passing through a nodal point of a projector lens.

47 Claims, 5 Drawing Sheets

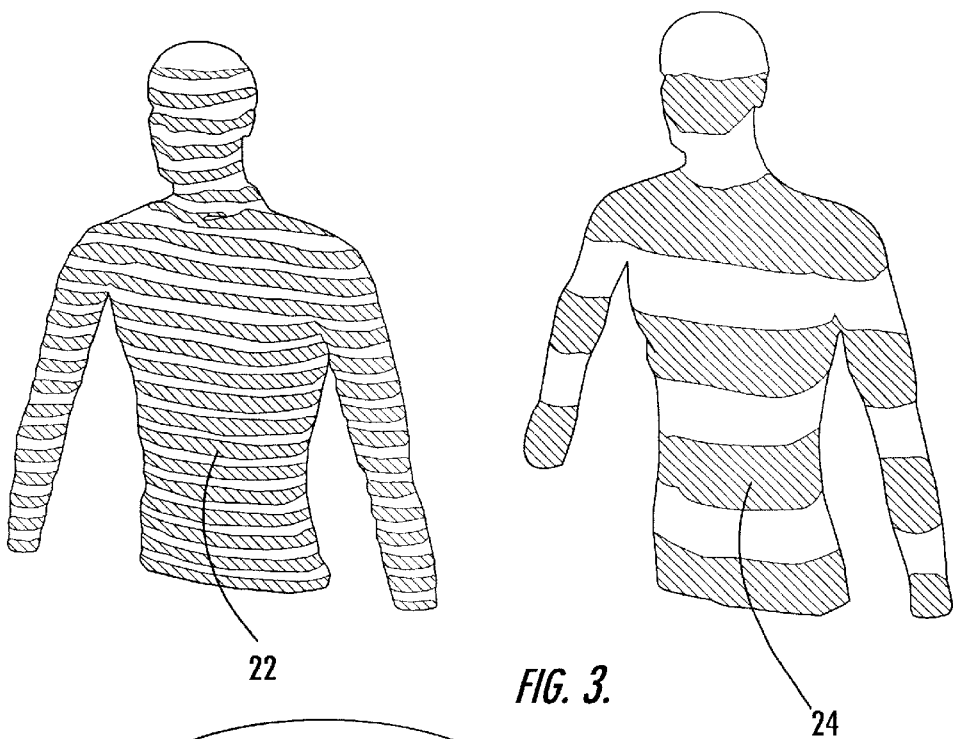
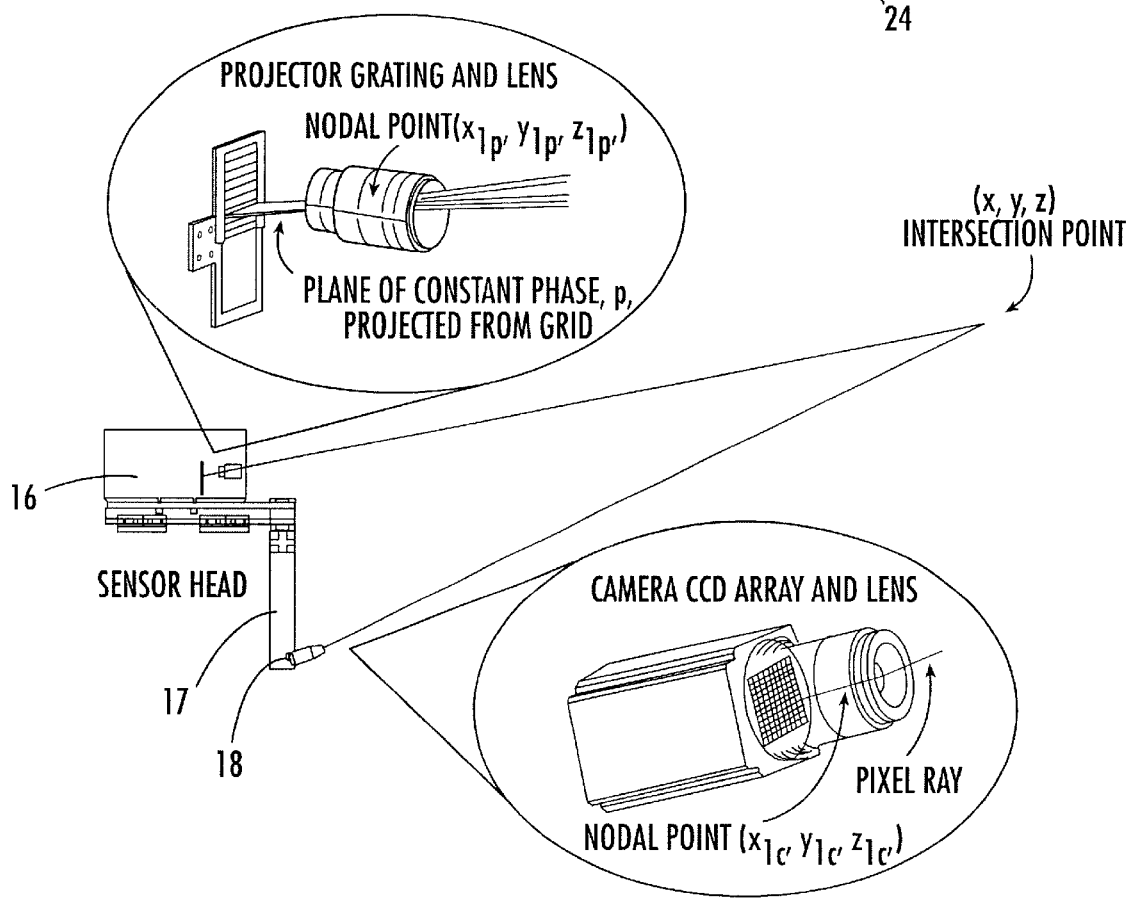
FIG. 3.
FIG. 4.

SYSTEMS, METHODS AND COMPUTER PROGRAM FOR MEASURING THE SURFACE CONTOUR OF AN OBJECT

This application claims benefit of U.S. provisional applicaton No. 60/073,776, filed Feb. 5, 1998.

FIELD OF THE INVENTION

The present invention relates generally to the measurement of contoured surfaces, and relates more specifically to the measurement of contoured surfaces with phase measurement profilometry (PMP).

BACKGROUND OF THE INVENTION

The apparel industry is moving toward mass customization in order to be more competitive. This move toward made-to-measure apparel requires underlying technology to facilitate acquiring human body measurements and extracting appropriate critical measurements so that apparel patterns can be selected and altered for the customer. Traditionally, tailors have taken these measurements themselves for their own pattern-altering methods. For this reason, a tailor's measurements can be very inconsistent when compared with other tailors. An accurate reliable data set of the surface of the body is needed in order to develop consistent body measurements.

Researchers have employed several technologies for body measurement, including two dimensional video silhouette images, laser-based scanning, and white light phase measurement. The white light phase measurement approach has proven to be a promising method of obtaining a full three-dimensional representation of the body without the use and cost of lasers. One example of the use of structured white light, phase measurement profilometry (PMP), is described in U.S. Pat. No. 4,641,972 to Halioua. The structured light and PMP application is well suited for body measurement because of the short acquisition time, accuracy and relatively low cost.

Unfortunately, the approach described in Halioua requires prior knowledge of the image field and continuity of the body surface. As a result, if discontinuities are present in the body surface to be measured, the Halioua method can be inaccurate. Discontinuities can occur if, for example,.the person being measured holds his arms against his sides. In this posture, the forwardmost surfaces of the arms are substantially farther from almost any sensor than those of the chest; yet, when the sensor detects the arms and chest at once, it has trouble differentiating that these objects are positioned at different depths. As a result, the measurement in this and other areas of discontinuity can be quite inaccurate.

One adaptation of the PMP approach is described in co-pending and co-assigned U.S. patent application Ser. No. 08/609,538 to Liang. In this method, after the sensors gather the image data of the body, points of discontinuity are identified by comparing the phase of the structured light at a particular point with the position of that point on a two-dimensional grid. If the point is sufficiently out of phase, it is identified as a point of discontinuity, and the processor that processes the data into three-dimensional information tracks this point as a discontinuity. Unfortunately, data analysis for this approach is heavy and thus can be somewhat slow.

SUMMARY OF THE INVENTION

In view of the above, it is an object of the present invention to provide a surface contour measurement system that can quickly and easily measure contoured surfaces such as the human body.

It is another object of the present invention to provide a surface contour measurement system that can detect and properly process discontinuities in the contoured surface.

These and other objects of the present invention are provided by systems, methods and computer program products for measuring, via a computing environment, the surface contour of a three-dimensional object, such as a human body, wherein two-dimensional deformed grating images are converted into three-dimensional data sets. The computing environment includes at least one sensor, computer storage for storing images captured by each sensor, and a data processor for processing images captured by each sensor and generating three-dimensional data sets. Each sensor includes a detector having a lens and an array of pixels for capturing images of the object. Each sensor also includes a projector having a lens and that is configured to project at least one grating pattern onto the surface of the object.

According to one embodiment of the present invention, a grating pattern, having a sinusoidally varying intensity pattern, is projected onto the surface of an object. The grating pattern varies in intensity sinusoidally in a vertical direction and is invariant in a horizontal direction. The grating pattern is referred to as a "coarse" grating pattern.

The projected coarse grating pattern is shifted, preferably four times, by a quarter (or other increment) of a period of the sinusoidally varying intensity pattern. At each shift, a two-dimensional deformed grating image of an area segment of the object surface is captured and stored. Inaccurate data, such as noise and phase measurement errors, are typically removed from the captured two-dimensional deformed grating images. A two-dimensional array of optical phase values is then created, wherein each optical phase value in the array corresponds with a respective pixel in the detector array of pixels.

Optical phase values in the two-dimensional array are then used to generate a plurality of three-dimensional data points that represent respective points on the surface of the object. Each three-dimensional data point corresponds with a respective pixel in the detector array of pixels. Each three-dimensional data point is found by locating, for each pixel in the detector array of pixels, a point on the surface of the object wherein a ray from a respective pixel passing through a nodal point of the detector lens is intersected by a plane of constant phase from the projected first grating pattern passing through a nodal point of the projector lens.

According to another aspect of the present invention, a coarse grating pattern having sinusoidally varying intensity pattern is projected onto an object, and then a "fine" grating pattern having a sinusoidally varying intensity pattern is projected onto the object. The fine grating pattern is selected so as to have a period less than that of the coarse grating pattern.

The projected coarse grating pattern is then shifted, preferably four times, and a plurality of two-dimensional deformed grating images are captured and stored as described above. A first two-dimensional array of optical phase values is then created, as described above. Next, the projected fine grating pattern is shifted, preferably four times, and a plurality of two-dimensional deformed grating images are captured and stored as described above. A second two-dimensional array of optical phase values is then created.

Three-dimensional data points that represent respective points on the surface of the object are then located by locating, for each pixel in a detector array of pixels, a point on the surface of the object wherein a first ray from a respective pixel passing through a nodal point of a detector lens is intersected by a first plane of constant phase from the projected coarse grating pattern passing through a nodal point of the projector lens. Then, for each pixel in the detector array of pixels, a point is located on the surface of the object wherein a second ray from a respective pixel passing through a nodal point of the detector lens is intersected by a second plane of constant phase from the projected fine grating pattern passing through a nodal point of the projector lens, wherein the second plane has a phase value within a predetermined range (e.g., between 0 and $\pi$) of phase values that includes a phase value of the first plane.

According to another aspect of the present invention, a scanning chamber for use in determining the surface contour of an object, such as a human body, is provided. A scanning chamber according to the present invention includes a frame having a central compartment and at least one compartment extending outwardly from, and in communication with, the central compartment. The frame is surrounded with a cover of non-reflective material, such as black cloth. An object for which the surface contour is to be determined is positioned within the central compartment. The central compartment preferably has a scanning volume of between about 1.5 cubic meters and about 3.5 cubic meters.

Scanning chambers according to the present invention may have various shapes and configurations. For example, a scanning chamber may have a Y-shaped configuration with three compartments extending outwardly from a central compartment. At least one sensor, and preferably two, is mounted within each outwardly extending compartment. Each sensor includes a detector having a lens and an array of pixels for capturing images of an object surface. Each sensor also includes a projector having a lens and that is configured to project at least one grating pattern onto the surface of the object.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 3 shows the fine and coarse grating projections produced by the projector of FIG. 2 on a subject.

FIG. 4 is a schematic illustration of the camera and projector of FIG. 2 demonstrating the correlation of structures therein to the mathematical model embodied in the software of the present invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

System

Figure 1:
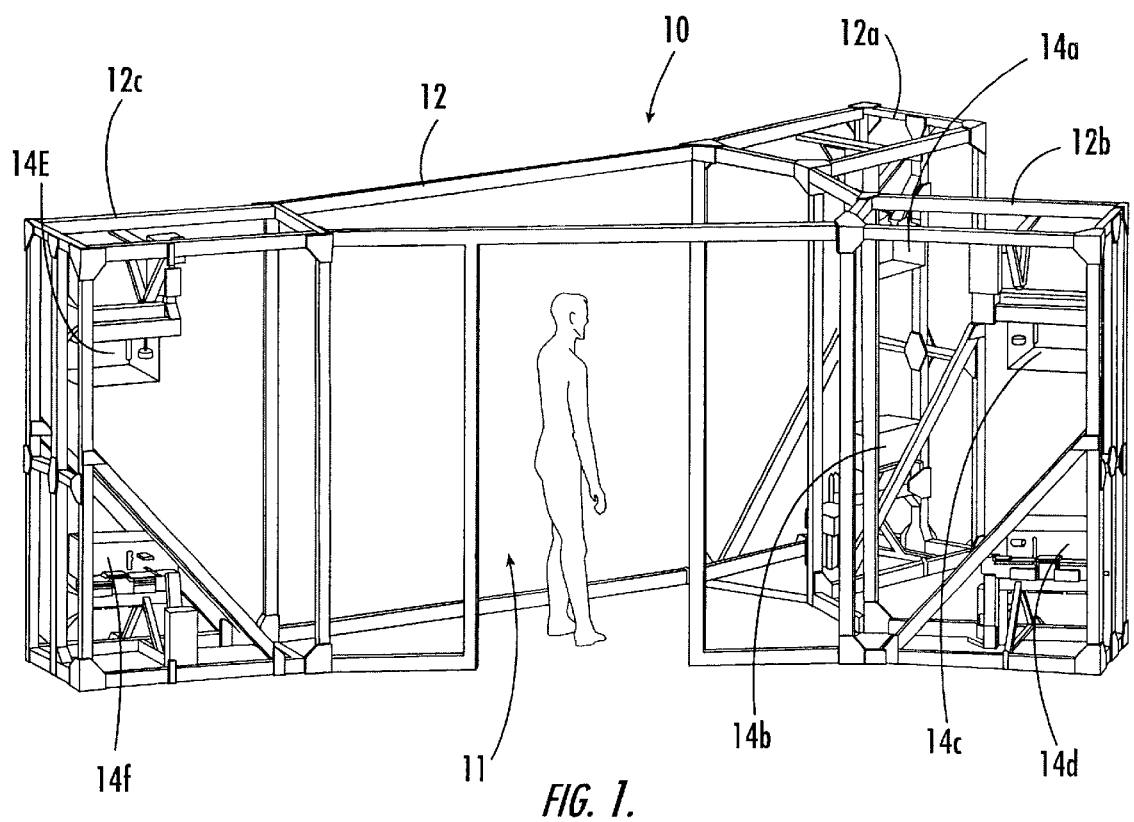
FIG. 1 is a perspective view of the body measurement system of the present invention.

Referring now to FIG. 1, a body measurement system, designated broadly at 10, is illustrated. The system 10 includes a scanning chamber 11, a series of six sensors 14a, 14b, 14c, 14d, 14e, 14f, and a controller (not shown). The scanning chamber 11 includes a generally Y-shaped frame 12 formed of black, anodized, extruded aluminum. The frame has two forward compartments 12a, 12b that are located in the "arms" of the "Y", and a rear compartment 12c located in the "tail" of the "Y". The "arms" of the "Y" define an angle of approximately 60 degrees with one another and an angle of about 150 degrees with the "tail" of the "Y". These angles enable optimal coverage of a human subject being measured.

A non-reflective black cloth (not shown) covers the frame 12 for-light tightness. On the floor of the chamber 11 are two footprints (not shown) or other indicators demonstrating where an occupant of the chamber 11 should stand and face during scanning; preferably, the footprints are positioned so that the occupant faces between the forward compartments 12a, 12b. This provides greater coverage of the front of the occupant, where greater detail is typically required. The frame 12 is sized such that a scanning volume (the volume within the chamber 11 that can be detected by the sensors 14a, 14b, 14c, 14d, 14e, 14f) is created having the dimensions 1.1m (wide), 1.0m (thickness), and 2.0 m (height).

The sensors 14a, 14b are mounted in the forward compartment 12a, the sensors 14c, 14d are mounted in the forward compartment 12b, and the sensors 14e, 14f are mounted in the rear compartment 12c. With the exception of their locations, the sensors 14a–14f are identical to one another; as such, only the sensor 14a will be described in detail herein; those skilled in this art will appreciate that the discussion is equally applicable to the other sensors.

The sensor 14a includes a projector 16 and a camera 18 mounted on a sensorhead frame 17. The projector 16 includes two gratings (not shown), the images of which can be projected onto an occupant of the chamber 11: a fine grating (e.g., 1 mm at the grating) that produces a fine grating pattern 22 on the occupant (see FIG. 3); and a coarse grating (e.g., 5 mm at the grating) that produces a coarse grating pattern 24 on the occupant (again, see FIG. 3). In either instance, the grating pattern varies in intensity sinusoidally in the vertical direction and is invariant in the horizontal direction.

An exemplary coarse grating pattern period may be between about 1 mm and about 30 mm at the grating. An exemplary fine grating pattern period may be between about 0.1 mm and about 5 mm at the grating. However, it is understood that the coarse and fine grating pattern periods may have other values as well. In any case, the period of the fine grating pattern will be less than the period of the coarse grating pattern.

The camera 18 can be any commercially available camera that can detect the pattern on the occupant and provide a signal corresponding to the image to the controller 20. The preferred camera 18 is a charge coupled device (CCD).

Figure 2:
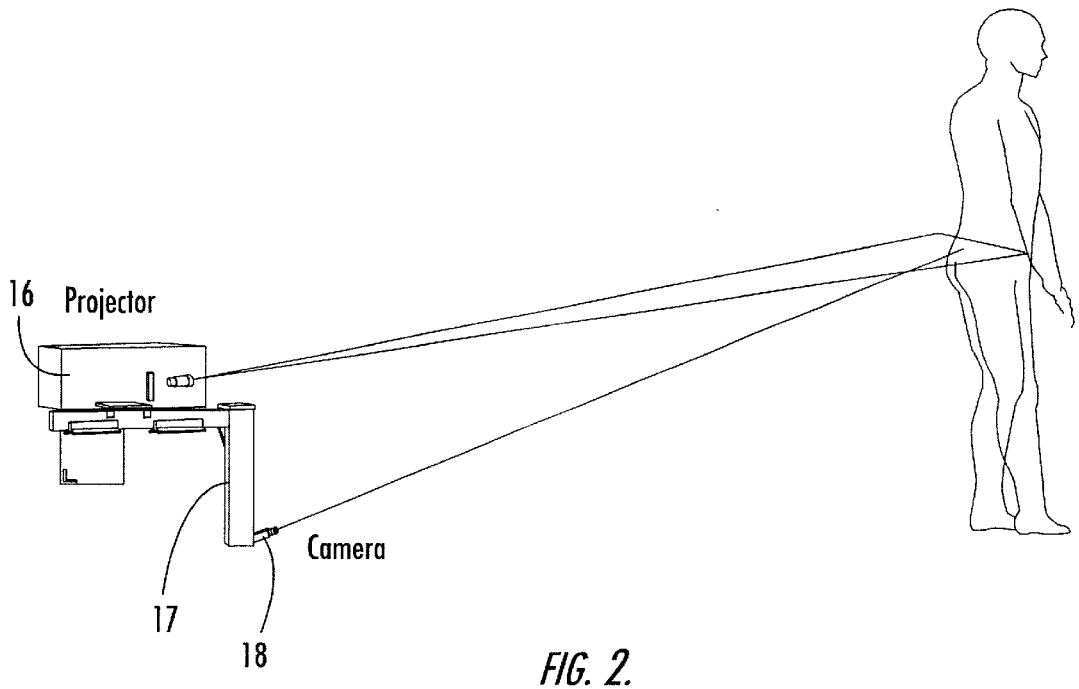
FIG. 2 is a schematic illustration of the triangulation formed between the camera and projector of the system of FIG. 1 and a subject being measured.

The projector 16 and the camera 18 are mounted rigidly on the sensorhead frame 17, which in turn is mounted in the frame 12, with the camera 18 being mounted below the projector 16. In this configuration, the camera 18 and projector 16 are separated by a baseline and thus form a triangulation with the occupant (see FIG. 2) that enables the distance to the projected image to be calculated.

Referring back to FIG. 1, the sensor 14a is mounted directly above the sensor 14b in the forward compartment 12a; similarly, the sensor 14c is mounted above the sensor 14d in the forward compartment 12b, and the sensor 14e is mounted above the sensor 14f in the rear compartment 12c. In this arrangement, an upper and a lower image can be obtained from each compartment to achieve total height coverage. Illustratively and preferably, sensors 14a, 14c, and 14e are mounted in an inverted position to provide a preferred camera angle.

All of the sensors 14a–14f are operatively connected to the controller, which in the illustrated embodiment is an Intel Pentium®-based personal computer with 128 MB of Random access memory. The controller also includes a motion control card and two frame grabber circuit boards. The controller is connected to both the projector 16 (to control the timing of projection) and to the camera 18 (to retrieve image data gathered by the camera 18) of each of the sensors 14a–14f.

The controller includes software that was developed in the Microsoft Developer Studio C++ language on a Windows NT platform. The software is configured to perform the following functions: providing a graphical user interface; controlling the data acquisition sequence; acquiring and storing image buffers; processing acquired images; calculating the resulting data points; and displaying graphical output (created in the OpenGL language). Of course, the software can be written in virtually any computer language known to be suitable for processing image data.

Phase Shifting

In operation, a person to be measured enters the scanning chamber 11 and places his feet on the designated footpads. Once the occupant is in place, scanning is initiated. The PMP method comprises projecting a grating pattern onto the occupant, recording the image, shifting the grating pattern in the direction of the varying phase, and capturing images at each position. A total of four images is taken for each sensor 14a–14f, each with the same amount of phase shift, $\pi/2$ radians, of the projected sinusoidal pattern. Using the four images of the scene, the phase at each pixel of the camera 18 can be determined. One advantage of the PMP method is that the phase value is independent of the ambient light level and the light output of the projector 18.

The general form of the projected pattern intensity is $$I(x,y)=R(x,y)[A(x,y)+B(x,y)\cos(p(x,y))] \qquad \text{(Equation II.A.1)}$$

where $R(x,y)$ is the object reflectivity, $A(x,y)$ represents the background intensity and $B(x,y)/A(x,y)$ the fringe contrast. When four equal phase shifts of 90 degrees are acquired, the resultant phase function of the intensities in the ideal case is given by $$p=\arctan[(I_4-I_2)/(I_1-I_3)] \qquad \text{(Equation II.A.2)}$$

As stated above, in each projector 16, two sinusoidal grating patterns are available: the fine grating pattern 22 and the coarse grating pattern 24. The fine grating 22 has a 1 mm period and can provide the required depth resolution of the data points. The coarse grating 24 has a 5 mm period and can provide gross depth information to resolve ambiguous phase data from the 1 mm grating.

Data Collection

As stated, four images for each sensor 14a–14f per grating pattern are acquired. Because there are six sensors 14a–14f in the system 10, a total of 24 images are captured for each grating pattern. In order to minimize the capture time, the controller acquires the images using a round robin acquisition scheme. In this manner, all of the images of the fine grating pattern 22 are captured in succession. Data collection for the 1 mm grating pattern 22 is captured within 2 seconds. This process continues until all 24 images have been acquired for the fine grating pattern 22.

After each sensor's image is acquired, the controller starts shifting the grating on each respective sensor 14a–14f so that the coarse grating pattern 24 can be projected. The round robin sequence is repeated with each of the sensors 14a–14f to acquire 24 images for the coarse grating pattern 24.

Calculation of Three-Dimensional Data Points

The phase information computed from the four images captured at each sensor for each grating pattern is used to calculate the three-dimensional data points. The calculated phase imaged by each pixel on the camera 18 is used to determine a specific line of constant phase on the grating pattern. A schematic of the sensor head with the projected plane and camera ray is shown in FIG. 4. The phase, p, is related to its spatial distance, $x_p$, on the grating by $$(p+2\pi \cdot m)=p_o+2\pi \cdot r_g \cdot x_p \qquad \text{(Equation II.C.1)}$$

where $p_o$ is the phase at x=0, $r_g$ is the spatial frequency of the sinusoidal pattern, and m is the $2\pi$ order with respect to x=0. This line of constant phase, at a distance $x_p$, when projected through the nodal point of the lens of the projector 16, $q_{lp}=(x_{lp}, y_{lp}, z_{lp})$, defines a unique plane in space. The equation of this plane is given by $$[z_{lp} \quad 0 \quad (x_p - x_{lp}) \quad -x_p z_{lp}] \begin{bmatrix} x \\ y \\ z \\ 1 \end{bmatrix} = 0 \qquad \text{(Equation II.C.2)}$$

A pixel location on the camera, $q_{cc}$, combined with the nodal point of the lens of the camera 18, $q_{lc}$, defines a unique ray in space.

$$\begin{bmatrix} x \\ y \\ z \\ 1 \end{bmatrix} = q_{cc} + k(q_{lc} - q_{cc}) \qquad \text{(Equation II.C.3)}$$

The parameter k traces points $q_s$ along the ray.

$$q_s = q_{cc} + k(q_{lc} - q_{cc}) \qquad \text{(Equation II.C.4)}$$

The intersection of the plane projected from the projector 18 and the ray from the camera pixel defines the parameter k. Substituting k back into Equation II.C.2 yields the (x,y,z) location of the imaged surface.

$$k = -\frac{(z_{lp}x_{cc} + (x_p - x_{lp})z_{cc} - x_p z_{lp})}{(z_{lp}(x_{lc} - x_{cc}) + (x_p - x_{lp})(z_{lc} - z_{cc}))}$$ (Equation II.C.5)

In Equation II.C.1 all of the variables are known except the order m. The order is determined using the coarse grating pattern 24 and the location of the scanning area. The coarse grating pattern 24 is coarse enough so that approximately one cycle (0 to $2\pi$), when projected, would span the depth of the scanning area. For each ray from the camera 18, all the possible phases that would fall in the scanning area can be determined. The calculated phase from the four images can then be mapped onto the camera ray, and the phase order is thereby determined. Once the order for the imaged phase on the coarse grating pattern 24 is determined, its $x_p$ location is calculated on the coarse grating. This $x_p$ location is then used to resolve the order of the phase for the fine grating pattern 22. The $x_p$ location on the coarse grating pattern 24 that was determined from the coarse scan should be very close to the $x_p$ location for the fine grating pattern 22. The fine order is determined from the coarse $x_p$ and the fine phase can be correctly mapped into this order, assuming that the difference between the coarse scan and the fine scan is no greater than $\pm\pi$.

Phase Measurement and Depth Solution Errors

As discussed above, for each sensor 14a–14f, one image is acquired for each of the four projected phase patterns for each grating pattern. The intensity values of these four images are processed at each pixel location to produce an estimate of the projected phase value at the corresponding imaged point on the subject. In contrast with edge-based pattern methods, such as that described in Grindon, J. R., "Non-contact 3-D Surface Digitization of the Human Head", Proceedings of the National Computer Graphics Association Annual Conference, Atlanta, April, 1989, the PMP method employs continuously varying amplitude patterns. The amplitude values convey the pattern information. Thus, the 3D depth measurement accuracy depends upon the accuracy of measuring the image pixel values. There are two potential sources of error in measuring the image pixel values: image noise and phase measurement error. These are discussed separately below.

Phase Error Standard Deviation Due to Image Noise

To find the phase measurement error standard deviation due to additive image noise, the noise is modeled as identically distributed, zero mean, uncorrelated random variables, $n_1$ through $n_4$ added to the respective image intensities, $I_1$ through $I_4$. Sources of this noise include quantization, granularity, and ensemble variations of the projected grating patterns themselves, as well as noise arising in the cameras 18 and image acquisition system 10. The analysis makes use of the fact that the body measurement system 10 is designed so that the noise standard deviation is small relative to the amplitude of the image signal.

Simplifying the notation of Equation II.A.1 without loss of generality, the four image signals at a given pixel can be modeled as $$I_1 = a + b\cos(p) + n_1$$ (Equation III.A.1a)

$$I_2 = a + b\cos(p + \pi/2) + n_2$$
$$= a - b\sin(p) + n_2$$ (Equation III.A.1b)

$$I_3 = a + b\cos(p + \pi) + n_3$$
$$= a - b\cos(p) + n_3$$ (Equation III.A.1c)

$$I_4 = a + b\cos(p + 3\pi/2) + n_4$$
$$= a + b\sin(p) + n_4$$ (Equation III.A.1d)

Two variables $I_5$ and $I_6$ can then be defined as:

$$I_5 = (I_1 - I_3)/2b$$
$$= \cos(p) + n_5$$ (Equation III.A.1e)

$$I_6 = (I_4 - I_2)/2b$$
$$= \sin(p) + n_6$$ (Equation III.A.1f)

Wherein the random variables $n_5$ and $n_6$ are independent and identically distributed, given by:

$$n_5 = (n_1 - n_3)/2b$$ (Equation III.A.2a)

$$n_6 = (n_4 - n_2)/2b$$ (Equation III.A.2b)

The phase can be estimated as p', where $$p' = \arctan(I_6/I_5)$$ (Equation III.A.3)

For relatively low noise levels (such as are expected here), p' can be modeled by a first order expansion as follows:

$$p' = p + n_6 \partial/\partial I_6 \arctan(I_6/I_5) + n_5 \partial/\partial I_5 \arctan(I_6/I_5)$$ (Eq.III.A.4)

As a result, the phase error, e, becomes:

$$e = p' - p$$
$$= (n_6 I_5 - n_5 I_6)/(I_5^2 + I_6^2)$$ (Equation III.A.5)

But since $$\cos^2(p) + \sin^2(p) = 1$$

the same first order approximation gives, $$I_5^2 + I_6^2 = 1$$ (Equation III.A.6)

and $$e = n_6 \cos(p) - n_5 \sin(p)$$ (Equation III.A.7)

The variance is the statistically expected value of the (zero mean) error squared:

$$\mathrm{var}(p) = E[e^2]$$
$$= E[n_6^2 \cos^2(p) - 2n_5 n_6 \sin(p)\cos(p) + n_5^2 \sin^2(p)]$$ (Equation III.A.8)

Because the pattern noises have been reasonably taken to be (a) statistically independent of the phase, (b) zero mean, and (c) statistically uncorrelated with one another, the expected value of the middle term is zero, and $$\mathrm{var}(p) = \cos^2(p) E[n_6^2] + \sin^2(p) E[n_5^2]$$ (Equation III.A.9)

Also, because they are identically distributed, with variance var(n,), it can be written that $$E[n_6^2] = E[n_5^2] \quad \text{(Equation III.A.10)}$$
$$= E[(n_1 - n_3)^2/4b^2]$$
$$= (1/4b^2)E[n_1^2 - 2n_1n_3 + n_3^2]$$
$$= (1/4b^2)(E[n_1^2] + E[n_3^2])$$
$$= \text{var}(n_0)/2b^2$$

Thus, the standard deviation of the phase error, std(p), is $$\text{std}(p) = \text{std}(n_0)/(b\sqrt{2}), \quad b \gg \text{std}(n_0) \quad \text{(Equation III.A.11)}$$

where std(p) is measured in radians. The sinusoidal pattern modulation amplitude, b, and the image noise standard deviation, std($n_0$), are in the same units. The value of b at a given pixel location in the image may be estimated as b' from the pixel values themselves, for the assumed low-noise condition using the relation $$b' = ((I_1-I_3)^2 + (I_2-I_4)^2)^{1/2}/2 \quad \text{(Equation III.A.12)}$$

Note that the phase error standard deviation varies inversely as the modulation amplitude b. Also, under the assumptions made, the phase error is independent of the phase value. This result is significant, for the phase error does not vary with the local slope of the sinusoidal pattern over the surface of the imaged subject. Thus, the method described exhibits a well behaved response to image noise.

A signal to noise ratio, SNR, can be defined at a given pixel location as the ratio of the variance of the sinusoidal pattern signal component, $b^2/2$, to the noise variance, var($n_0$):

$$\text{SNR} = b^2/(2\text{var}(n_0)) \quad \text{(Equation III.A.13)}$$

The phase error standard deviation can be expressed in terms of the SNR:

$$\text{std}(p) = 1/(2\sqrt{\text{SNR}}), \text{rad}, \text{SNR} \gg 1 \quad \text{(Equation III.A.14)}$$

Depth Solution Error Due to Phase Measurement Error

Figure 5:
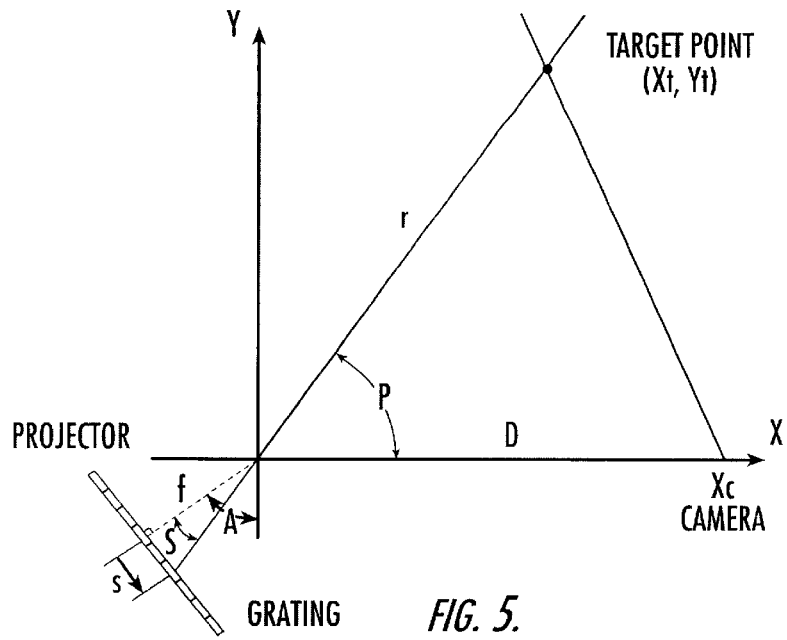
FIG. 5 is a graph illustrating the geometry used to calculate the proper depth of surfaces on a subject.

The effect of a phase measurement error is to produce an error in the solution for the target point position, or depth, along the ray defined by the camera lens nodal point and the modeled position of the pixel in 3D space. This is illustrated in FIG. 5, which shows the relevant geometry projected onto an (x, y) plane. For analysis, the coordinates are defined as follows: the origin of the (x, y, z) coordinate system is defined at the projector lens nodal point; the x axis is defined to pass through the camera lens nodal point at $x_c$; and the (x, y) plane is defined to pass through the target point at ($x_t$, $y_t$).

The projector 16 is modeled as a sinusoidal grating at an inclination angle of A with respect to the x axis, positioned at a perpendicular distance, (or focal length, f) from the lens nodal point. In practice, the grating is normally constructed to be invariant along one axis, and oriented so that the invariant axis is nominally parallel to the z axis as the coordinates are defined here. Thus, in FIG. 5, the invariant axis of the grating is perpendicular to the paper. The grating pattern varies sinusoidally along its length in the plane of the paper.

When a phase measurement is made, the solution model computes the distance, s, of the projected phase line along the grating from the point where a perpendicular line passes through the lens. If the pitch of the sinusoidal grating is $r_g$ periods per millimeter, and the measured phase is p radians, then this distance is, in millimeters, $$s = p/(2\pi r_g) \quad \text{(Equation III.B.1)}$$

The ray passing through the projector lens at the origin from the point at distance s along the grating—which is in the (x, y) plane because for this analysis the target point is in the (x, y) plane—defines a line at an angle P with respect to the x axis (FIG. 5).

An angle S is formed by this geometry where $$S = \arctan(s/f) \quad \text{(Equation III.B.2)}$$

The angle P is related to angles A and S by $$P = S + A + \pi/2 \quad \text{(Equation III.B.3)}$$

The effect of a phase measurement error, dp, is to produce an error dP in the solution for the angle P. First, the projector constant c can be defined as, $$c = 2\pi f r_g \quad \text{(Equation III.B.4)}$$

Substituting first Equation III.B.1 and then Equation III.B.4 into Equation III.B.2, gives $$S = \arctan(p/c) \quad \text{(Equation III.B.5)}$$

This constant has units of radians, and is a measure of the fineness of the projected pattern. The error in angle P caused by a phase measurement error dp is then, for small errors, found by taking the partial derivative of the angle P with respect to the phase p as follows:

$$dP = (c/(c^2 + p^2))dp \quad \text{(Equation III.B.6)}$$

where the phase, p, can be expressed in terms of the angle P as $$i \ p = c \ \cot(A - P) \quad \text{(Equation III.B.7)}$$

The standard deviation of the angle P is $$\text{std}(P) = (c/(c^2 + p^2)) \ \text{std}(p) \quad \text{(Equation III.B.8)}$$

Equation III.B.6 provides the error in angle P that is caused by a phase error dp. This is expressed in terms of the angle P, the grating inclination A, the projector lens focal length f, and the grating pitch in periods per millimeter, $r_g$. It remains to find the depth error along the camera ray.

Referring again to FIG. 5, the ray through the projector lens is described by $$y = x \tan(P) \quad \text{(Equation III.B.9)}$$

and the ray through the camera lens by $$y = y_t((x - x_c)/(x_t - x_c)) \quad \text{(Equation III.B.10)}$$

Defining r as the range from the projector lens to the target, and using the substitutions in Equations III.B.9 and III.B.10, $$x_t = r \cos(P) \quad Y_t = r \sin(P) \quad \text{(Equation III.B.11)}$$

and taking partial derivatives, the x and y errors in the target point solution, dx and dy, produced by an angle error dP, are found to be, under the reasonable assumption of small errors, $$dx = (r^2 (\cos(P) - x_c/r)/x_c \sin(P))dP \quad \text{(Equation III.B.12)}$$

$$dy=(r^2/x_c)dP \quad \text{(Equation III.B.13)}$$

D can be defined as the baseline distance between the projector and the camera, i.e. $D=x_c$. The standard deviation of the depth error is $$\text{std(depth)}=\text{std}(P)(r^2/D)(1+((\cos(P)-D/r)/\sin(P))^2)^{1/2} \quad \text{(Equation III.B.14)}$$

Note the $r^2/D$ range dependence of depth error for $r>>D$. This is characteristic of triangulation-based depth measurement systems. For this analysis, the target point is defined to be in the (x, y) plane and the grating is taken to be aligned so that it is invariant with z. Thus, the target point is centered, and no z-error is caused by an error in angle P. More generally, the target point will not be centered and there will be an error in z. In normal practice, the z error (perpendicular to the paper in FIG. 5) is small compared to the depth error calculated using these equations.

Figure 6:
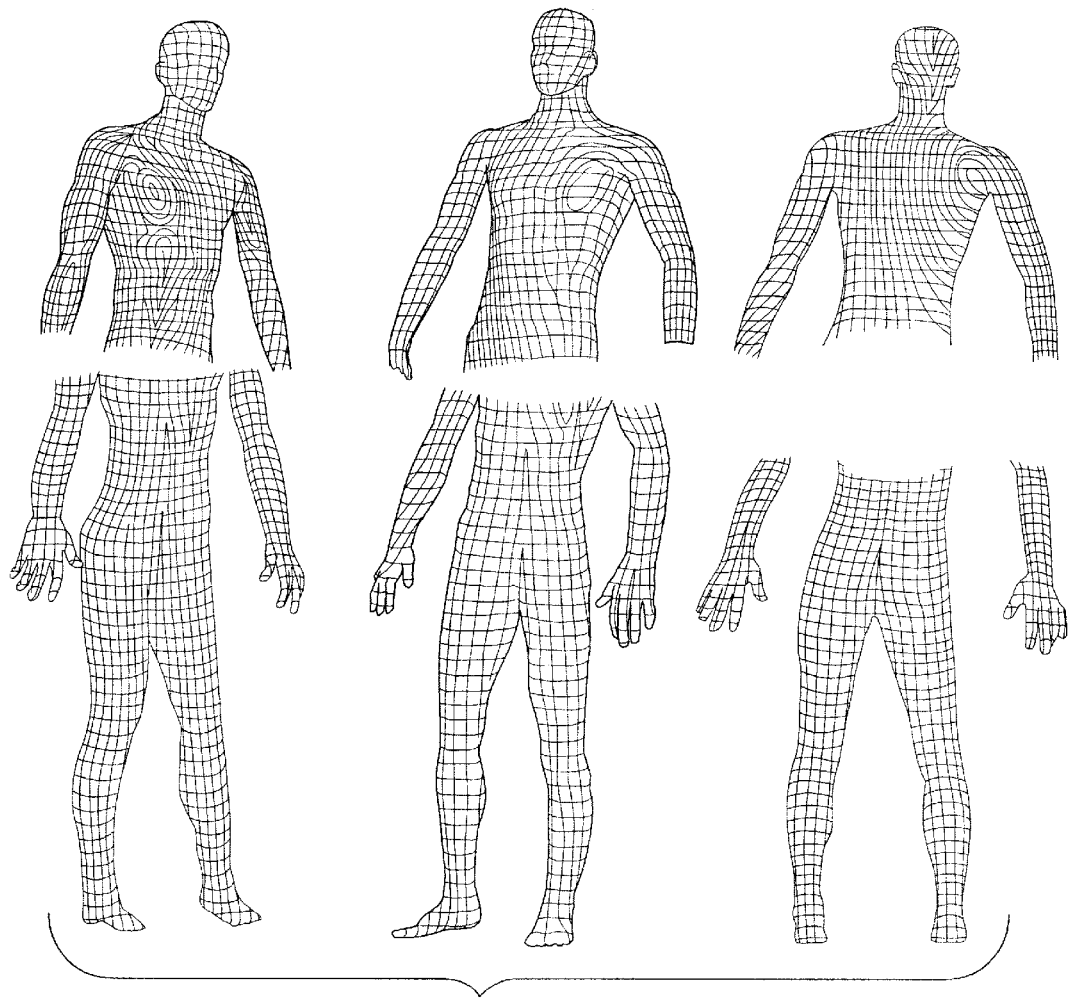
FIG. 6 shows six individual view of three-dimensional data points, one of which corresponds to each of the six sensors of the system of FIG. 1.
Figure 7:
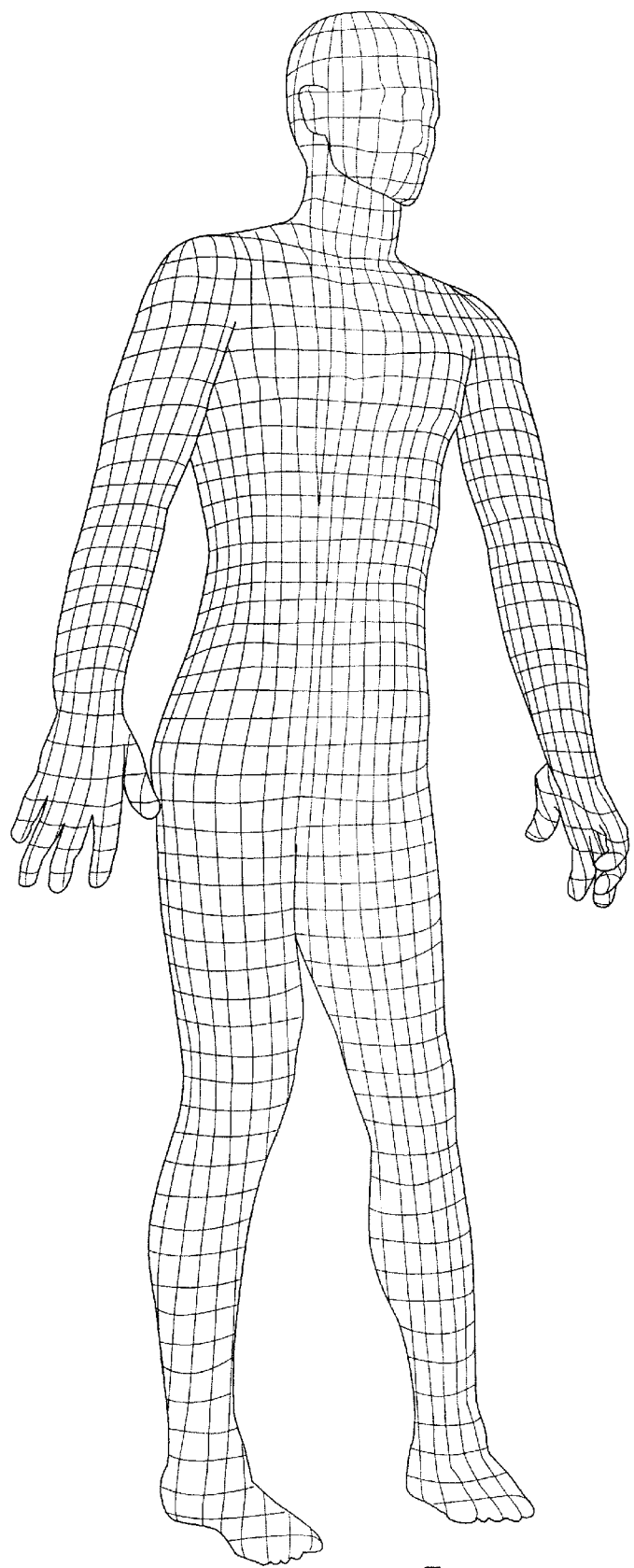
FIG. 7 is a three-dimensional composite data set compiled by the body measurement system of the FIG. 1.

The intermediate output of the PMP process is a data cloud for each of the six views (see FIG. 6). These data clouds are combined such that the resultant output is an accurate composite point cloud (FIG. 7). The individual views are combined by knowing the exact orientation of each view with respect to one other. Their orientation is derived by calibrating the sensors 14a–14f.

By scanning a calibration object of known size and orientation, the orientation of each sensor can be calculated with respect to the object. By placing the calibration object approximately where the subject will be standing, a coarse correlation between the object and the subject to be scanned can be obtained. This is important not only to assure correct coverage but to make sure the subject is within the depth of focus of each of the sensors 14a–14f.

During system calibration, the calibration object is acquired using the acquisition sequence described above. Once the images have been acquired, they are processed and the resulting data points are determined with these data points being maintained in sensor coordinates (FIG. 6). The system calibration process takes the area segment that is visible to each sensor and matches it to the calibration object using a minimization routine. Once the orientation of each sensor head has been determined, a transformation matrix is developed to transform the data into global coordinates. FIG. 7 shows the resultant composite data set of a mannequin that was scanned with the BMS system 10. These data points are the raw calculated points without any smoothing or other post-processing.

Operations

The present invention is described below with reference to flowchart illustrations of methods, apparatus (systems) and computer program products according to an embodiment of the invention. It will be understood that each block of the flowchart illustrations, and combinations of blocks in the flowchart illustrations, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Figure 8:
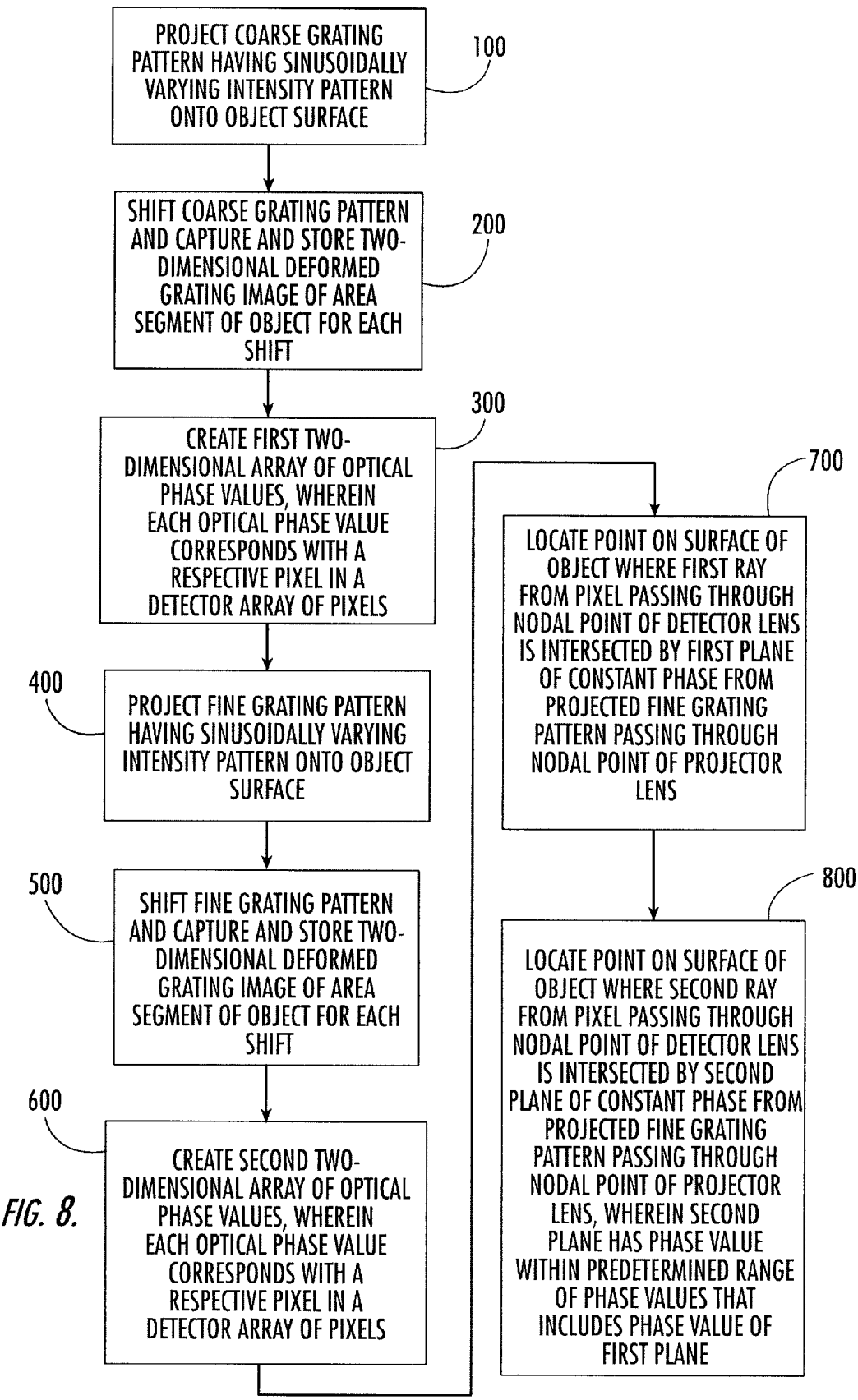
FIG. 8 schematically illustrates operations according to the present invention for obtaining a three-dimensional data set that is representative of a surface of a three-dimensional object.

Referring now to FIG. 8, operations according to the present invention for obtaining a three-dimensional data set that is representative of a surface of a three-dimensional object are illustrated. A coarse grating pattern having a sinusoidally varying intensity pattern is projected onto the surface of an object (Block 100). The coarse grating pattern is shifted by a predetermined portion of the period of its pattern and a two-dimensional deformed grating image of an area segment of the object is captured and stored for each shift (Block 200). A first two-dimensional array of optical phase values is created, wherein each optical phase value in the first array corresponds with a respective pixel in a detector array of pixels (Block 300).

A fine grating pattern having a sinusoidally varying intensity pattern is then projected onto the surface of the object (Block 400). The fine grating pattern is also shifted by a predetermined portion of the period of its pattern and a two-dimensional deformed grating image of the same area segment of the object is captured and stored for each shift (Block 500). A second two-dimensional array of optical phase values is created, wherein each optical phase value in the second array corresponds with a respective pixel in a detector array of pixels (Block 600).

Optical phase values in the first and second two-dimensional arrays are then used to generate a plurality of three-dimensional data points that represent respective points on the surface of the object. For each pixel in the detector array of pixels, a point on the surface of the object is located wherein a first ray from a respective pixel passing through a nodal point of the detector lens is intersected by a first plane of constant phase from the projected coarse grating pattern passing through a nodal point of the projector lens (Block 700). Then, for each pixel in the detector array of pixels, a point is located on the surface of the object wherein a second ray from a respective pixel passing through a nodal point of the detector lens is intersected by a second plane of constant phase from the projected fine grating pattern passing through a nodal point of the projector lens, wherein the second plane of constant phase has a phase value within a predetermined range of phase values that includes a phase value of the first plane of constant phase (Block 800).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of obtaining, via a computing environment, a three-dimensional data set that is representative of a surface of a three-dimensional object, wherein the computing environment includes at least one sensor, storage means for storing images captured by each sensor, and processing means for processing images captured by each sensor, wherein the at least one sensor comprises a detector having a lens and an array of pixels for capturing images of the object, and a projector having a lens and that is configured to project first and second grating patterns onto the surface of the object, wherein the first grating pattern has a sinusoidally varying intensity pattern period that is longer than a sinusoidally varying intensity pattern period of the second grating pattern, the method comprising the steps of:

projecting the first grating pattern onto the surface of the object;

capturing and storing a first plurality of two-dimensional deformed grating images of an area segment of the object surface, wherein each of the first plurality of two-dimensional deformed grating images are shifted, relative to each other, by a predetermined portion of the period of the first sinusoidally varying intensity pattern;

creating a first two-dimensional array of optical phase values, wherein each optical phase value in the first array corresponds with a respective pixel in the detector array of pixels;

projecting the second grating pattern onto the surface of the object;

capturing and storing a second plurality of two-dimensional deformed grating images of the area segment of the object surface, wherein each of the second plurality of two-dimensional deformed grating images are shifted, relative to each other, by a predetermined portion of the period of the second sinusoidally varying intensity pattern;

creating a second two-dimensional array of optical phase values, wherein each optical phase value in the second array corresponds with a respective pixel in the detector array of pixels; and using optical phase values in the first and second two-dimensional arrays to generate a plurality of three-dimensional data points that represent respective points on the surface of the object, wherein each three-dimensional data point corresponds with a respective pixel in the detector array of pixels.

2. A method according to claim 1 wherein the step of using optical phase values in the first and second two-dimensional arrays to generate a plurality of three-dimensional data points that represent respective points on the surface of the object comprises:

locating, for each pixel in the detector array of pixels, a point on the surface of the object wherein a first ray from a respective pixel passing through a nodal point of the detector lens intersects a first plane of constant phase from the projected first grating pattern passing through a nodal point of the projector lens; and locating, for each pixel in the detector array of pixels, a point on the surface of the object wherein a second ray from a respective pixel passing through a nodal point of the detector lens intersects a second plane of constant phase from the projected second grating pattern passing through a nodal point of the projector lens, wherein the second plane of constant phase has a phase value within a predetermined range of phase values that includes a phase value of the first plane of constant phase.

3. A method according to claim 2 wherein the predetermined range of phase values is between 0 and $\pi$.

4. A method according to claim 1 further comprising the step of removing inaccurate data from the captured first and second plurality of two-dimensional deformed grating images.

5. A method according to claim 4 wherein the step of removing inaccurate data from the captured first and second plurality of two-dimensional deformed grating images comprises the steps of:

removing noise from the captured first and second plurality of two-dimensional deformed grating images; and removing phase measurement errors from the captured first and second plurality of two-dimensional deformed grating images.

6. A method according to claim 1 wherein the first and second grating patterns vary in intensity sinusoidally in a vertical direction and are invariant in a horizontal direction.

7. A method according to claim 1 wherein the captured first plurality of two-dimensional deformed grating images are shifted, relative to each other, by a quarter of the period of the first sinusoidally varying intensity pattern, and wherein the second captured plurality of two-dimensional deformed grating images are shifted, relative to each other, by a quarter of the period of the second sinusoidally varying intensity pattern.

8. A method according to claim 1 wherein the first grating pattern has a sinusoidally varying intensity pattern period of between about 1 millimeters and about 30 millimeters.

9. A method according to claim 1 wherein the second grating pattern has a sinusoidally varying intensity pattern period of between about 0.1 millimeters and about 5 millimeters.

10. A method according to claim 1 wherein the at least one sensor comprises a plurality of sensors circumferentially spaced around the object.

11. A method according to claim 1 wherein the step of capturing and storing a first plurality of two-dimensional deformed grating images of an area segment of the object surface comprises capturing and storing at least three two-dimensional deformed grating images of an area segment of the object surface, and wherein the step of capturing and storing a second plurality of two-dimensional deformed grating images of an area segment of the object surface comprises capturing and storing at least three two-dimensional deformed grating images of an area segment of the object surface.

12. A system for obtaining a three-dimensional data set that is representative of a surface of a three-dimensional object, comprising:

at least one sensor comprising:

a projector having a lens and configured to project first and second grating patterns onto the surface of the object, wherein the first grating pattern has a sinusoidally varying intensity pattern period that is longer than a sinusoidally varying intensity pattern period of the second grating pattern, and wherein the projector is configured to shift the first and second grating patterns by a predetermined portion of a respective period of the first and second sinusoidally varying intensity patterns; and a detector having a lens and an array of pixels for capturing a first plurality of two-dimensional deformed grating images of an area segment of the object surface, wherein each of the first plurality of two-dimensional deformed grating images are shifted, relative to each other, by a predetermined portion of a period of the first sinusoidally varying intensity pattern, and for capturing a second plurality of two-dimensional deformed grating images of an area segment of the object surface, wherein each of the second plurality of two-dimensional deformed grating images are shifted, relative to each other, by a predetermined portion of a period of the second sinusoidally varying intensity pattern;

means for storing the captured first and second plurality of two-dimensional deformed grating images;

means for creating a first two-dimensional array of optical phase values, wherein each optical phase value in the first array corresponds with a respective pixel in the detector array of pixels;

means for creating a second two-dimensional array of optical phase values, wherein each optical phase value in the second array corresponds with a respective pixel in the detector array of pixels; and means for using optical phase values in the first and second two-dimensional arrays to generate a plurality of three-dimensional data points that represent respective points on the surface of the object, wherein each three-dimensional data point corresponds with a respective pixel in the detector array of pixels.

13. A system according to claim 12 wherein the means for using optical phase values in the first and second two-dimensional arrays to generate a plurality of three-dimensional data points that represent respective points on the surface of the object comprises:

means for locating, for each pixel in the detector array of pixels, a point on the surface of the object wherein a first ray from a respective pixel passing through a nodal point of the detector lens intersects a first plane of constant phase from the projected first grating pattern passing through a nodal point of the projector lens; and means for locating, for each pixel in the detector array of pixels, a point on the surface of the object wherein a second ray from a respective pixel passing through a nodal point of the detector lens intersects a second plane of constant phase from the projected first grating pattern passing through a nodal point of the projector lens, wherein the second plane of constant phase has a phase value within a predetermined range of phase values that includes a phase value of the first plane of constant phase.

14. A system according to claim 13 wherein the predetermined range of phase values is between 0 and $\pi$.

15. A system according to claim 12 further comprising means for removing inaccurate data from the captured first and second plurality of two-dimensional deformed grating images.

16. A system according to claim 15 wherein the means for removing inaccurate data from the captured first and second plurality of two-dimensional deformed grating images comprises:

means for removing noise from the captured first and second plurality of two-dimensional deformed grating images; and means for removing phase measurement errors from the captured first and second plurality of two-dimensional deformed grating images.

17. A system according to claim 12 wherein the first and second grating patterns vary in intensity sinusoidally in a vertical direction and are invariant in a horizontal direction.

18. A system according to claim 12 wherein the captured first plurality of two-dimensional deformed grating images are shifted, relative to each other, by a quarter of the period of the first sinusoidally varying intensity pattern, and wherein the second captured plurality of two-dimensional deformed grating images are shifted, relative to each other, by a quarter of the period of the second sinusoidally varying intensity pattern.

19. A system according to claim 12 wherein the first grating pattern has a sinusoidally varying intensity pattern period of between about 1 millimeters and about 30 millimeters.

20. A system according to claim 12 wherein the second grating pattern has a sinusoidally varying intensity pattern period of between about 0.1 millimeters and about 5 millimeters.

21. A system according to claim 12 wherein the at least one sensor comprises a plurality of sensors circumferentially spaced around the object.

22. A system for determining a surface contour of an object, comprising:

a scanning chamber, comprising:
a frame comprising a central compartment and at least one compartment extending outwardly from, and in communication with, the central compartment, wherein the object is positioned within the central compartment; and
a cover surrounding the frame;

a first sensor mounted within the at least one compartment, wherein the first sensor comprises:
a first projector having a lens and configured to project a first grating pattern onto the surface of the object, wherein the first grating pattern has a first sinusoidally varying intensity pattern, and
wherein the first projector is configured to shift the first grating pattern by a predetermined portion of a period of the first sinusoidally varying intensity pattern; and
a first detector having a lens and an array of pixels for capturing a first plurality of two-dimensional deformed grating images of an area segment of the object surface, wherein each of-the first plurality of two-dimensional deformed grating images are shifted, relative to each other, by a predetermined portion of a period of the first sinusoidally varying intensity pattern;

means for storing the captured first plurality of two-dimensional deformed grating images;

means for creating a two-dimensional array of optical phase values, wherein each optical phase value in the array corresponds with a respective pixel in the first detector array of pixels; and means for using optical phase values in the two-dimensional array to generate a plurality of three-dimensional data-points that represent respective points on the surface of the object, wherein each three-dimensional data point corresponds with a respective pixel in the first detector array of pixels.

23. A system according to claim 22 wherein the means for using optical phase values in the two-dimensional array to generate a plurality of three-dimensional data points that represent respective points on the surface of the object comprises means for locating, for each pixel in the first detector array of pixels, a point on the surface of the object wherein a ray from a respective pixel passing through a nodal point of the first detector lens intersects a plane of constant phase from the projected first grating pattern passing through a nodal point of the first projector lens.

24. A system according to claim 22 further comprising means for removing inaccurate data from the captured first plurality of two-dimensional deformed grating images.

25. A system according to claim 22 wherein the means for removing inaccurate data from the captured first plurality of two-dimensional deformed grating images comprises:

means for removing noise from the captured first plurality two-dimensional deformed grating. images; and means for removing phase measurement errors from the captured first plurality of two-dimensional deformed grating images.

26. A system according to claim 22 wherein the first grating pattern varies in intensity sinusoidally in a vertical direction and is invariant in a horizontal direction.

27. A system according to claim 22 wherein the captured first plurality of two-dimensional deformed grating images are shifted, relative to each other, by a quarter of a period of the first sinusoidally varying intensity pattern.

28. A system according to claim 22 wherein the first sinusoidally varying intensity pattern has a period of between about 1 millimeters and about 5 millimeters.

29. A system according to claim 22 further comprising:

a second sensor mounted within the at least one compartment, wherein the second sensor comprises:

a second projector having a lens and configured to project a first grating pattern onto the surface of the object, wherein the first grating pattern has a first sinusoidally varying intensity pattern, and wherein the second projector is configured to shift the first grating pattern by a predetermined portion of a period of the first sinusoidally varying intensity pattern; and is a second detector having a lens and an array of pixels for capturing a second plurality of two-dimensional deformed grating images of an area segment of the object surface, wherein each of the second plurality of two-dimensional deformed grating images are shifted, relative to each other, by a predetermined portion of a period of the first sinusoidally varying intensity pattern;

means for storing the captured second plurality of two-dimensional deformed grating images;

means for creating a two-dimensional array of optical phase values, wherein each optical phase value in the array corresponds with a respective pixel in the second detector array of pixels; and means for using optical phase values in the two-dimensional array to generate a plurality of three-dimensional data points that represent respective points on the surface of the object, wherein each three-dimensional data point corresponds with a respective pixel in the second detector array of pixels.

30. A system according to claim 29 wherein the means for using optical phase values in the two-dimensional array to generate a plurality of three-dimensional data points that represent respective points on the surface of the object comprises, means for locating, for each pixel. in the second detector array of pixels, a point on the surface of the object wherein a ray from a respective pixel passing through a nodal point of the second detector lens is intersected by a plane of constant phase from the projected first grating pattern passing through a nodal point of the second projector lens.

31. A system according to claim 22 wherein the at least one compartment comprises a plurality of compartments, each compartment extending outwardly from, and in communication with, the central compartment, and wherein each compartment includes at least one sensor mounted therewithin, wherein each sensor comprises:

a projector having a lens and configured to project a grating pattern onto the surface of the object, wherein the grating pattern has a sinusoidally varying intensity pattern, and wherein the projector is configured to shift the grating pattern by a predetermined portion of a period of the sinusoidally varying intensity pattern; and a detector having a lens and an array of pixels for capturing a plurality of two-dimensional deformed grating images of an area segment of the object surface, wherein each of the plurality of two-dimensional deformed grating images are shifted, relative to each other, by a predetermined portion of a period of the sinusoidally varying intensity pattern.

32. A system according to claim 31 wherein the scanning chamber comprises a Y-shaped frame comprising a central compartment and first, second and third compartments extending outwardly from, and in communication with, the central compartment, and wherein the first, second and third compartments each includes at least one sensor mounted therewithin, wherein each sensor comprises:

a projector having a lens and configured to project a grating pattern onto the surface of the object, wherein the grating pattern has a sinusoidally varying intensity pattern, and wherein the projector is configured to shift the grating pattern by a predetermined portion of a period of the sinusoidally varying intensity pattern; and a detector having a lens and an array of pixels for capturing a plurality of two-dimensional deformed grating images of an area segment of the object surface, wherein each of the plurality of two-dimensional deformed grating images are shifted, relative to each other, by a predetermined portion of a period of the sinusoidally varying intensity pattern.

33. A system according to claim 32 wherein the first and second compartments define an angle of about 60 degrees with one another and an angle of about 150 degrees with the third compartment.

34. A system according to claim 22 further comprising means for rotating the object within the central compartment.

35. A system according to claim 22 wherein the cover is formed from non-reflective material.

36. A system according to claim 22 wherein the object is a human body.

37. A system according to claim 22 wherein the central compartment has a scanning volume of between about 1.5 cubic meters and about 3.5 cubic meters.

38. A computer program product for obtaining, via a computing environment, a three-dimensional data set that is representative of a surface of a three-dimensional object, wherein the computing environment includes at least one sensor, storage means for storing images captured by each sensor, and processing means for processing images captured by each sensor, wherein the at least one sensor comprises a detector having a lens and an array of pixels for capturing images of the object, and a projector having a lens and that is configured to project first and second grating patterns onto the surface of the object, wherein the first grating pattern has a sinusoidally varying intensity pattern period that is longer than a sinusoidally varying intensity pattern period of the second grating pattern, the computer program product comprising a computer usable storage medium having computer readable program code means embodied in the medium, the computer readable program code means comprising:

computer readable program code means for projecting the first grating pattern onto the surface of the object;

computer readable program code means for capturing and storing a first plurality of two-dimensional deformed grating images of an area segment of the object surface, wherein each of the first plurality of two-dimensional deformed grating images are shifted, relative to each other, by a predetermined portion of the period of the first sinusoidally varying intensity pattern;

computer readable program code means for creating a first two-dimensional array of optical phase values, wherein each optical phase value in the first array corresponds with a respective pixel in the detector array of pixels;

computer readable program code means for projecting the second grating pattern onto the surface of the object;

computer readable program code means for capturing and storing a second plurality of two-dimensional deformed grating images of the area segment of the object surface, wherein each of the second plurality of two-dimensional deformed grating images are shifted, relative to each other, by a predetermined portion of the period of the second sinusoidally varying intensity pattern;

computer readable program code means for creating a second two-dimensional array of optical phase values, wherein each optical phase value in the second array corresponds with a respective pixel in the detector array of pixels; and computer readable program code means for using optical phase values in the first and second two-dimensional arrays to generate a plurality of three-dimensional data points that represent respective points on the surface of the object, wherein each three-dimensional data point corresponds with a respective pixel in the detector array of pixels.

39. A computer program product according to claim 38 wherein the computer readable program code means for using optical phase values in the first and second two-dimensional arrays to generate a plurality of three-dimensional data points that represent respective points on the surface of the object comprises:

computer readable program code means for locating, for each pixel in the detector array of pixels, a point on the surface of the object wherein a first ray from a respective pixel passing through a nodal point of the detector lens intersects a first plane of constant phase from the projected first grating pattern passing through a nodal point of the projector lens; and computer readable program code means for locating, for each pixel in the detector array of pixels, a point on the surface of the object wherein a second ray from a respective pixel passing through a nodal point of the detector lens intersects a second plane of constant phase from the projected first grating pattern passing through a nodal point of the projector lens, wherein the second plane of constant phase has a phase value within a predetermined range of phase values that includes a phase value of the first plane of constant phase.

40. A computer program product according to claim 39 wherein the predetermined range of phase values is between 0 and $\pi$.

41. A computer program product according to claim 39 further comprising computer readable program code means for removing inaccurate data from the captured first and second plurality of two-dimensional deformed grating images.

42. A computer program product according to claim 41 wherein the computer readable program code means for removing inaccurate data from the captured first and second plurality of two-dimensional deformed grating images comprises:

computer readable program code means for removing noise from the captured first and second plurality of two-dimensional deformed grating images; and computer readable program code means for removing phase measurement errors from the captured first and second plurality of two-dimensional deformed grating images.

43. A computer program product according to claim 38 wherein the first and second grating patterns vary in intensity sinusoidally in a vertical direction and are invariant in a horizontal direction.

44. A computer program product according to claim 38 wherein the captured first plurality of two-dimensional deformed grating images are shifted, relative to each other, by a quarter of the period of the first sinusoidally varying intensity pattern, and wherein the second captured plurality of two-dimensional deformed grating images are shifted, relative to each other, by a quarter of the period of the second sinusoidally varying intensity pattern.

45. A computer program product according to claim 38 wherein the first grating pattern has a sinusoidally varying intensity pattern period of between about 1 millimeters and about 30 millimeters.

46. A computer program product according to claim 38 wherein the second grating pattern has a sinusoidally varying intensity pattern period of between about 0.1 millimeters and about 5 millimeters.

47. A computer program product according to claim 38 wherein the computer readable program code means for capturing and storing a first plurality of two-dimensional deformed grating images of an area segment of the object surface comprises computer readable program code means for capturing and storing at least three two-dimensional deformed grating images of an area segment of the object surface, and wherein the computer readable program code means for capturing and storing a second plurality of two-dimensional deformed grating images of an area segment of the object surface comprises computer readable program code means for capturing and storing at least three two-dimensional deformed grating images of an area segment of the object surface.

* * * * *

UNITED STATES PATENT AND TRADEMARK OFFICE
CERTIFICATE OF CORRECTION

PATENT NO.    : 6,373,963 B1
DATED         : April 16, 2002
INVENTOR(S)   : Demers et al.

It is certified that error appears in the above-identified patent and that said Letters Patent is hereby corrected as shown below:

<u>Title page,</u>
Item [54], The title should read as follows:
-- SYSTEMS, METHODS AND COMPUTER PROGRAM PRODUCTS FOR MEASURING THE SURFACE CONTOUR OF AN OBJECT --

Signed and Sealed this

Twenty-fourth Day of September, 2002

*Attest:*

JAMES E. ROGAN
*Attesting Officer*            *Director of the United States Patent and Trademark Office*